United States Patent
Douglas et al.

(10) Patent No.: US 6,749,589 B1
(45) Date of Patent: Jun. 15, 2004

(54) SUBCUTANEOUS INJECTION SET FOR USE WITH A RESERVOIR THAT HAS A SEPTUM

(75) Inventors: Joel Douglas, Los Altos Hills, CA (US); Robert Hugo, Gilroy, CA (US)

(73) Assignee: Sterling Medications, Inc., Norcross, GA (US)

( * ) Notice: Subject to any disclaimer, the term of this patent is extended or adjusted under 35 U.S.C. 154(b) by 67 days.

(21) Appl. No.: 09/675,159

(22) Filed: Sep. 29, 2000

Related U.S. Application Data
(60) Provisional application No. 60/195,702, filed on Apr. 7, 2000, provisional application No. 60/188,624, filed on Mar. 13, 2000, and provisional application No. 60/176,538, filed on Jan. 18, 2000.

(51) Int. Cl.[7] ........................ A61M 5/178; A61M 37/00; A61M 5/32
(52) U.S. Cl. ........................... 604/165.01; 604/164.08; 604/162
(58) Field of Search .................. 604/200, 201, 604/205, 164.01, 165.03, 165.01, 177, 263, 164.07, 264, 600, 564, 567, 604, 272, 174, 890.1, 157, 170, 164.11, 198, 164.08, 195, 136, 187, 606, 164.12, 164.06, 505, 569, 185, 171

(56) References Cited

U.S. PATENT DOCUMENTS

| | | |
|---|---|---|
| 3,502,097 A | 3/1970 | Muller |
| 3,861,972 A | 1/1975 | Glover et al. |
| 3,986,508 A | 10/1976 | Barrington |
| 4,235,234 A | 11/1980 | Whitney et al. |
| 4,352,354 A | 10/1982 | Ujihara |
| 4,352,358 A | 10/1982 | Angelchik |
| 4,362,156 A | 12/1982 | Feller, Jr. et al. |
| 4,511,359 A | 4/1985 | Vaillancourt |
| 4,531,937 A | 7/1985 | Yates |
| 4,619,643 A | 10/1986 | Bai |
| 4,664,656 A | 5/1987 | Taddei |
| 4,713,057 A * | 12/1987 | Huttner et al. ......... 604/164.07 |
| 4,723,947 A | 2/1988 | Konopka |
| 4,752,292 A | 6/1988 | Lopez et al. |
| 4,755,173 A | 7/1988 | Konopka et al. |
| 4,834,149 A | 5/1989 | Fournier et al. |
| 4,863,432 A | 9/1989 | Kvalo |
| 4,944,728 A | 7/1990 | Carrell et al. |
| 5,176,662 A | 1/1993 | Bartholomew et al. |

(List continued on next page.)

FOREIGN PATENT DOCUMENTS

| | | |
|---|---|---|
| EP | 0 256694 A1 | 2/1988 |
| EP | 0 268 480 A1 | 5/1988 |
| EP | 0 363 953 A2 | 4/1990 |
| EP | 0 451 040 A1 | 10/1991 |
| WO | WO 88/03816 | 6/1988 |

(List continued on next page.)

*Primary Examiner*—Brian L. Casler
*Assistant Examiner*—Roz Maiorino
(74) *Attorney, Agent, or Firm*—Burns Doane Swecker & Mathis L.L.P.

(57) ABSTRACT

An infusion set includes a needle hub with a needle to be inserted in a through passageway of the cannula housing through a sealing surface of a soft cannula. The infusion set includes a guide for centering the needle relative to the cannula sealing surface, a dirt trap, and the through passageway, as well as a locking device for locking the cannula housing and the needle hub together to prevent inadvertent disengagement. The guide includes co-operating guide pins and guide openings and a draft angle on the needle hub. The pins are located on each side of the needle and the through passageway. The connecting tube includes an inner tube of polyethylene and shrink fitted tubing at each end suitable for a solvent bonding layer. The composite can be reinforced with monofilament strands sandwiched between the two tubular layers to prevent kinking, or the inner tube can be formed in a triangular shape. The triangular shape composite is incased in a thin polyester shrink tube.

3 Claims, 10 Drawing Sheets

U.S. PATENT DOCUMENTS

| | | | |
|---|---|---|---|
| 5,186,712 A | * 2/1993 | Kelso et al. | ............... 604/157 |
| 5,267,967 A | 12/1993 | Schneider | |
| 5,338,314 A | 8/1994 | Ryan | |
| 5,344,414 A | 9/1994 | Lopez | |
| 5,423,775 A | 6/1995 | Cannon | |
| 5,487,728 A | 1/1996 | Vaillancourt | |
| 5,501,676 A | 3/1996 | Niedospial et al. | |
| 5,507,733 A | 4/1996 | Larkin et al. | |
| 5,514,117 A | 5/1996 | Lynn | |
| 5,522,803 A | 6/1996 | Teissen-Simony | |
| 5,637,098 A | 6/1997 | Bierman | |
| 5,688,254 A | 11/1997 | Lopez et al. | |
| 5,702,371 A | 12/1997 | Bierman | |
| 5,718,682 A | 2/1998 | Tucker | |
| 5,722,959 A | 3/1998 | Bierman | |
| 5,735,271 A | 4/1998 | Lorenzen et al. | |
| 5,776,116 A | 7/1998 | Lopez et al. | |
| 5,810,781 A | 9/1998 | Bierman | |
| 5,954,643 A | 9/1999 | VanAntwerp et al. | |
| 5,954,708 A | 9/1999 | Lopez et al. | |
| 5,968,011 A | 10/1999 | Larsen et al. | |
| 5,971,950 A | 10/1999 | Lopez et al. | |
| 5,980,506 A | 11/1999 | Mathiasen | |
| 6,056,718 A | 5/2000 | Funderburk et al. | |
| 6,086,575 A | 7/2000 | Mejslov | |
| 6,109,259 A | 8/2000 | Fitzgerald | |
| 6,123,690 A | 9/2000 | Mejslov | |
| 6,142,446 A | 11/2000 | Leinsing | |
| 6,213,996 B1 | 4/2001 | Jepson et al. | |
| 6,290,688 B1 | 9/2001 | Lopez et al. | |
| 6,302,866 B1 | 10/2001 | Marggi | |
| 6,371,943 B1 | * 4/2002 | Racz et al. | ............... 604/264 |

FOREIGN PATENT DOCUMENTS

| | | |
|---|---|---|
| WO | 97/37713 | 10/1997 |
| WO | 98/41384 | 9/1998 |
| WO | 99/44655 | 9/1999 |

* cited by examiner

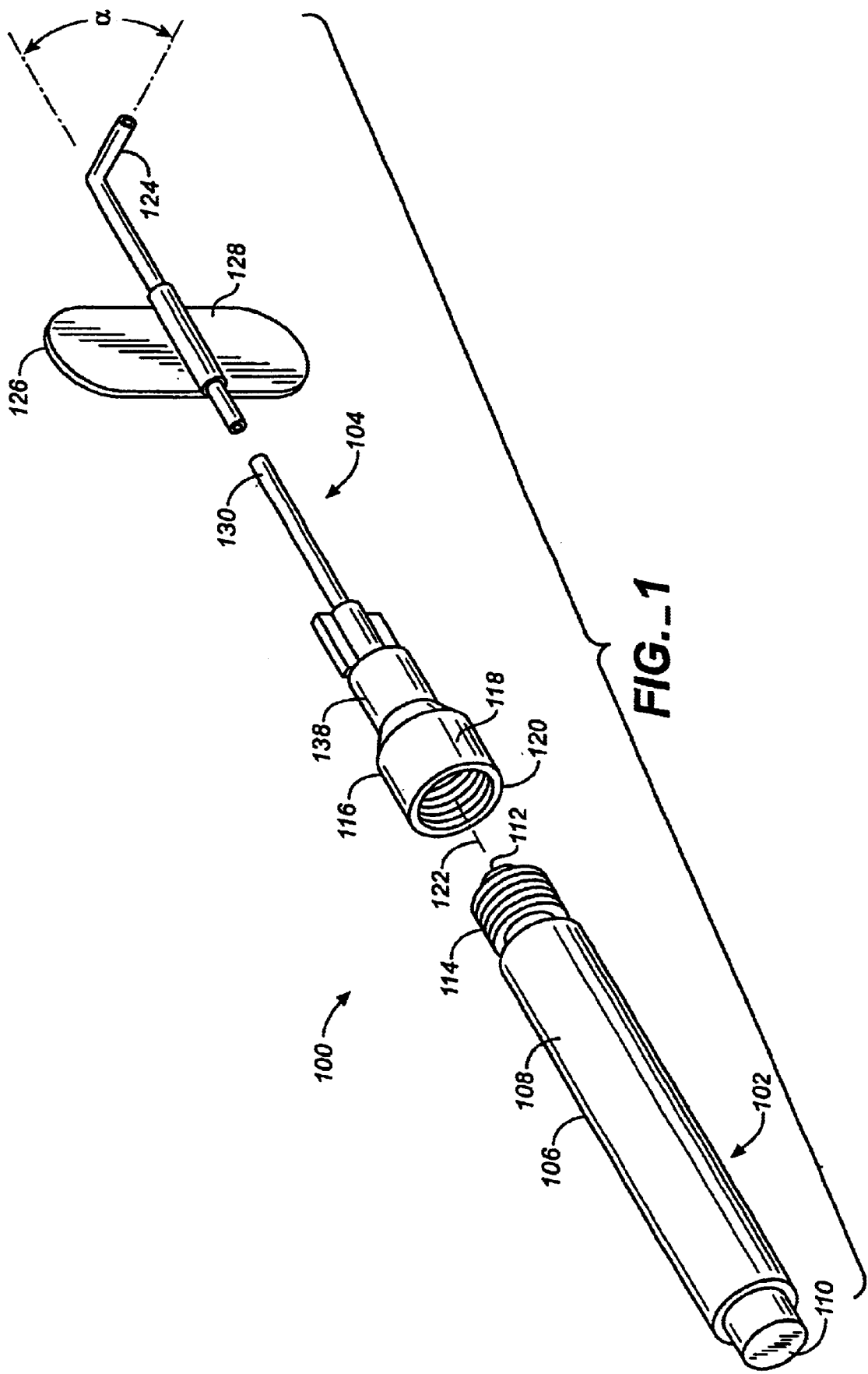
FIG._1

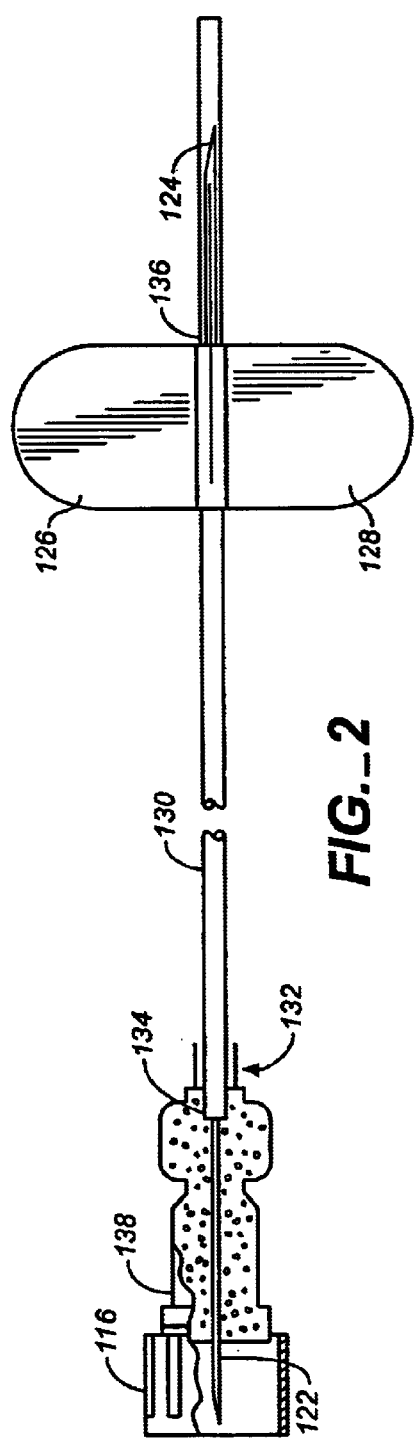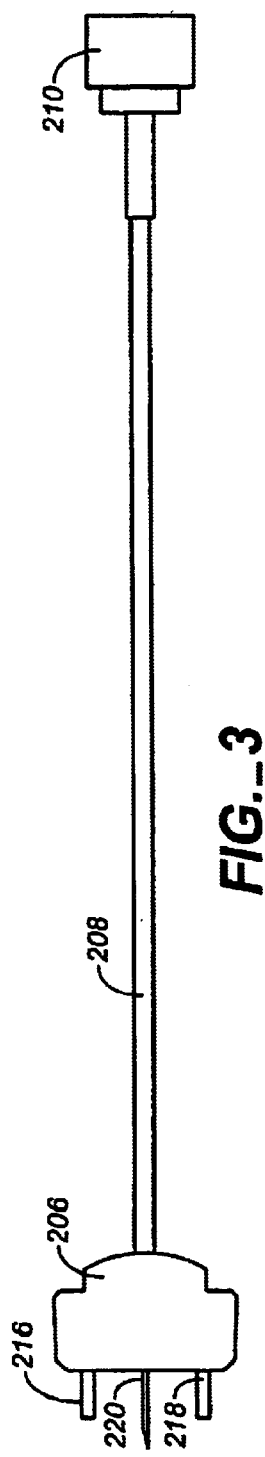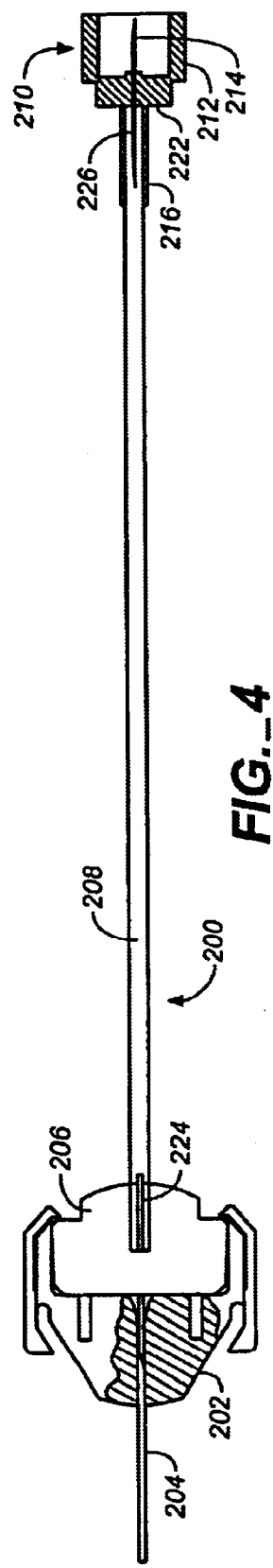

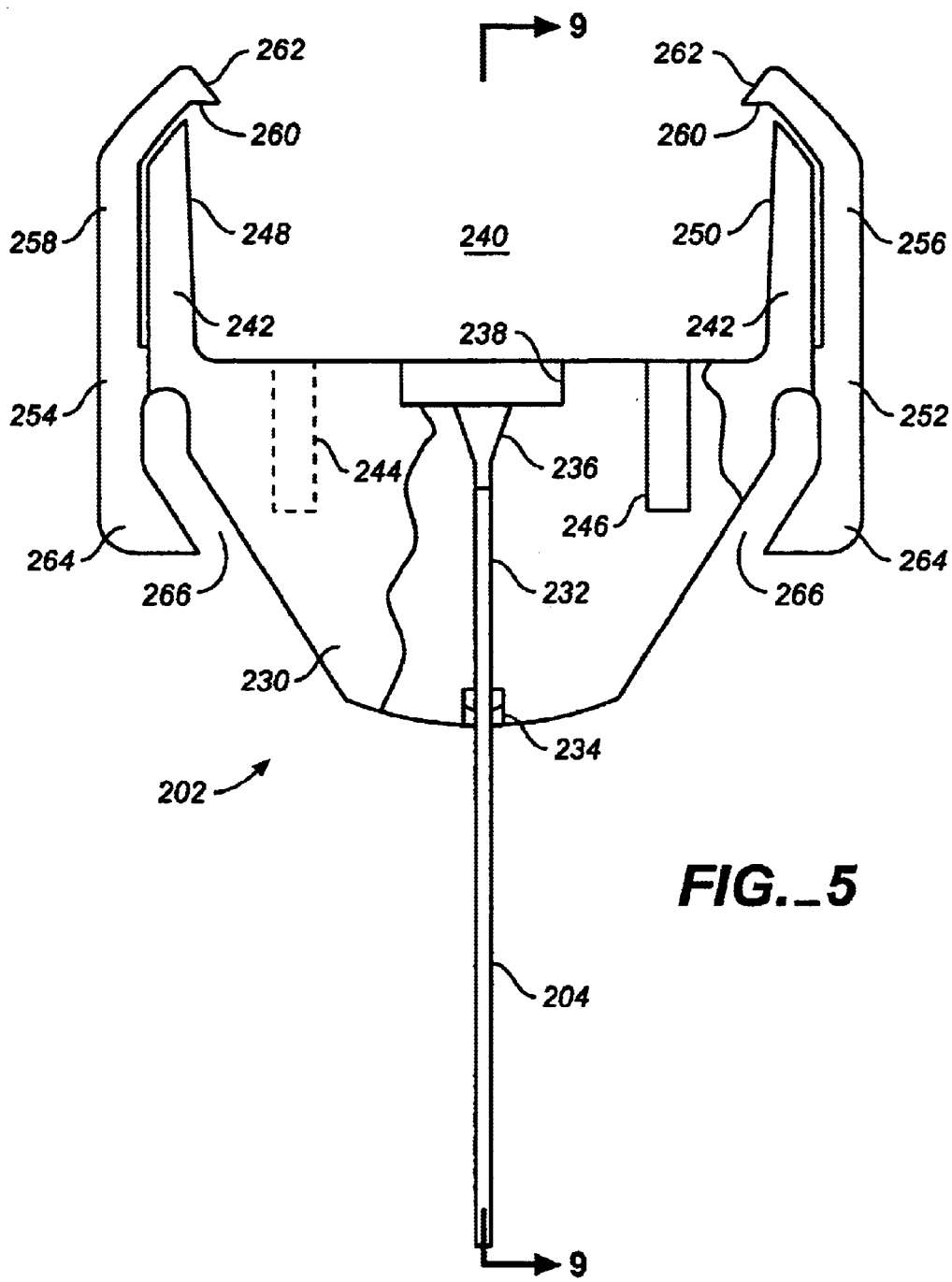
FIG._5
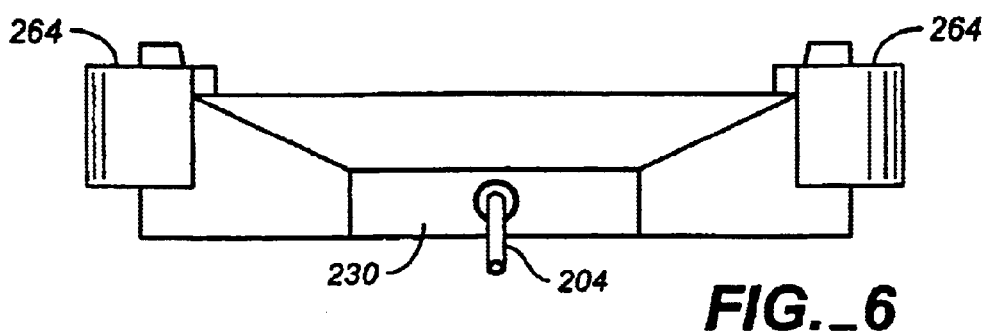
FIG._6

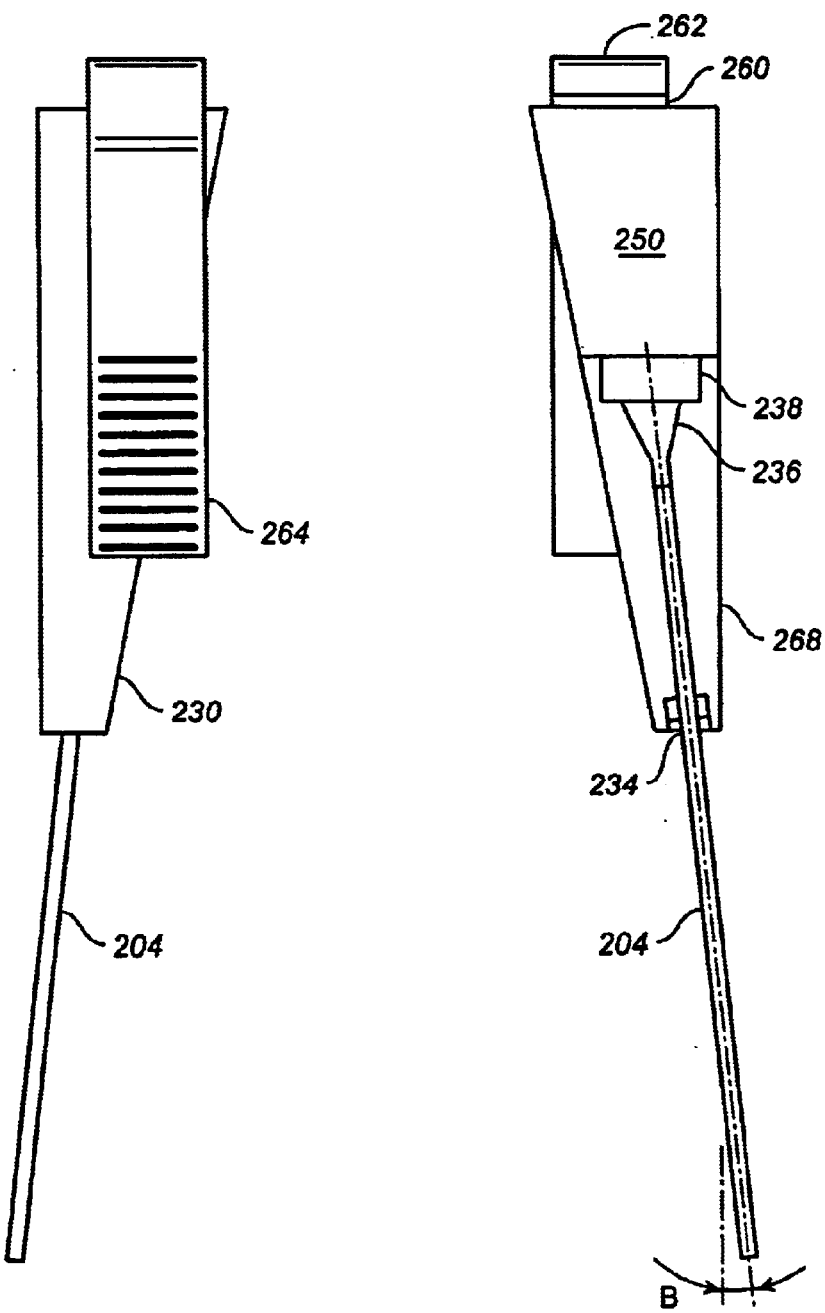

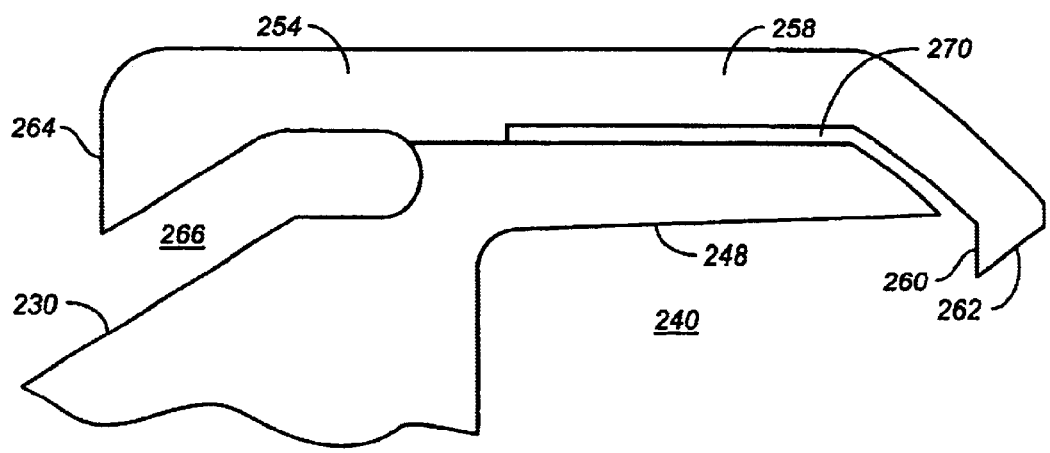
FIG._10
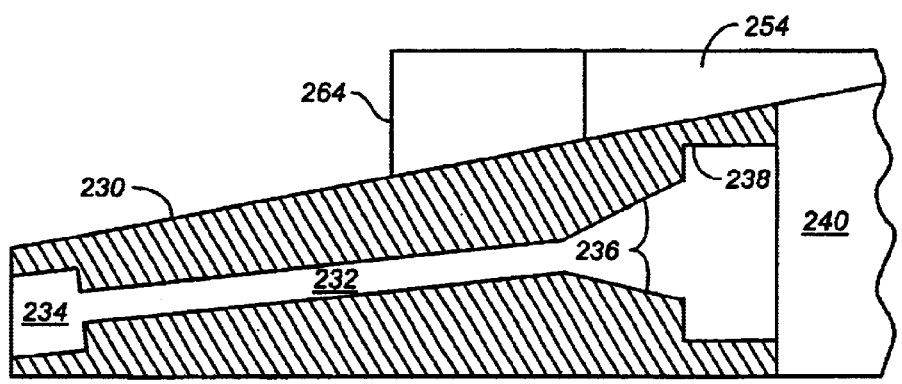
FIG._11

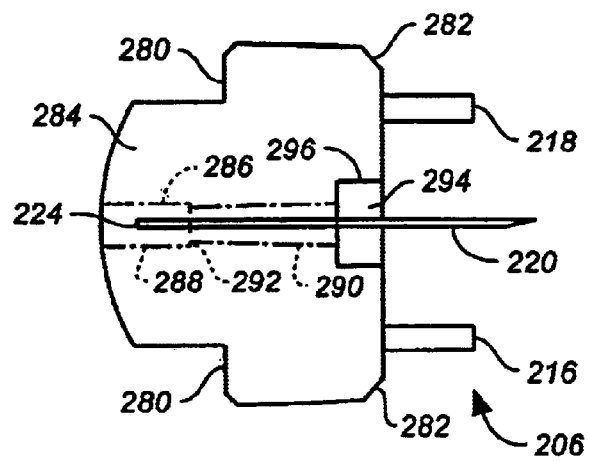
FIG._12
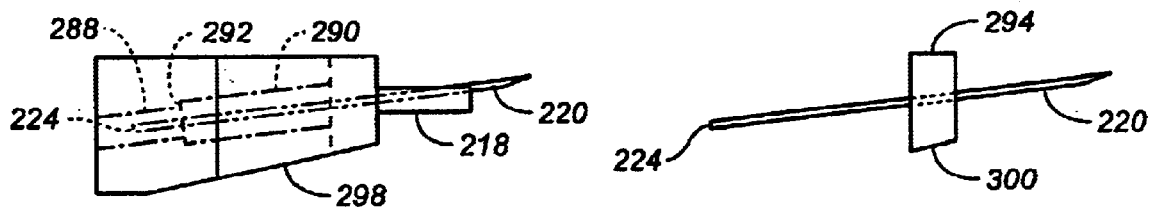
FIG._13                FIG._13A
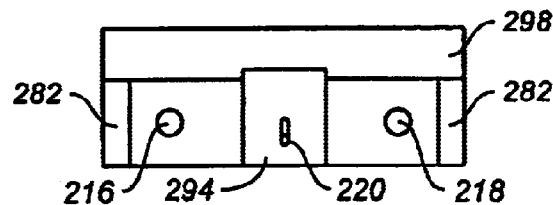
FIG._14

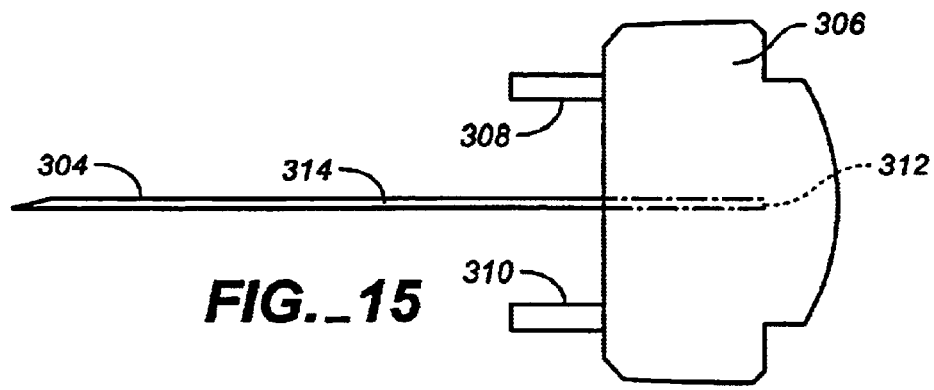
FIG._15
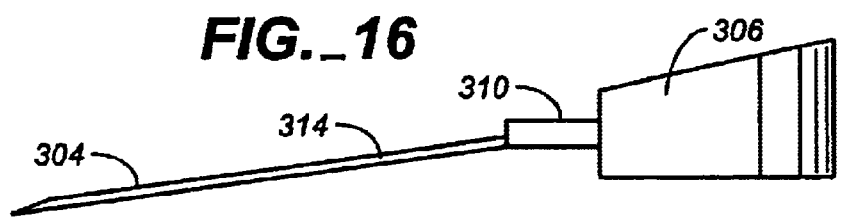
FIG._16
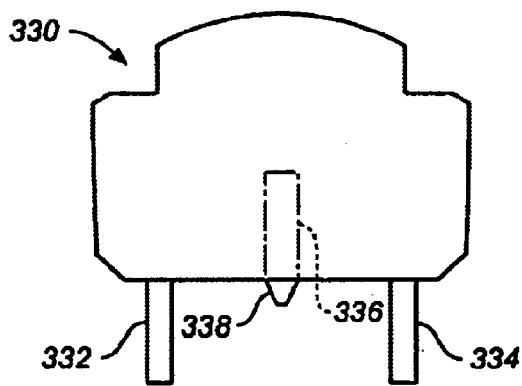
FIG._17
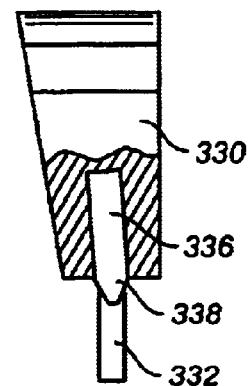
FIG._19
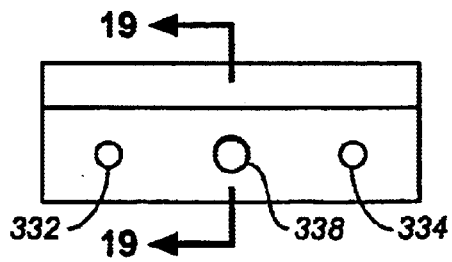
FIG._18

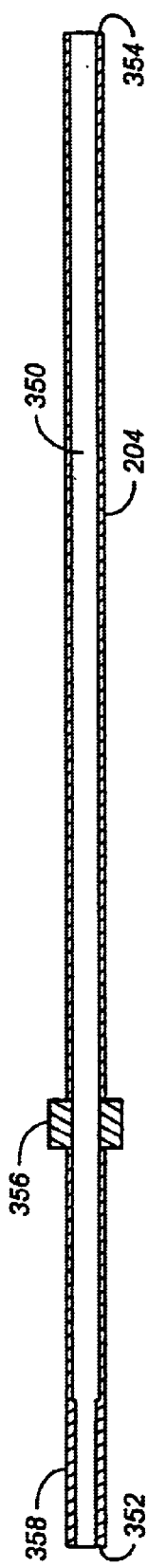
FIG._20
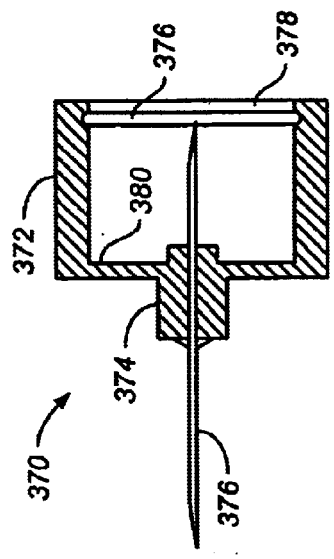
FIG._22
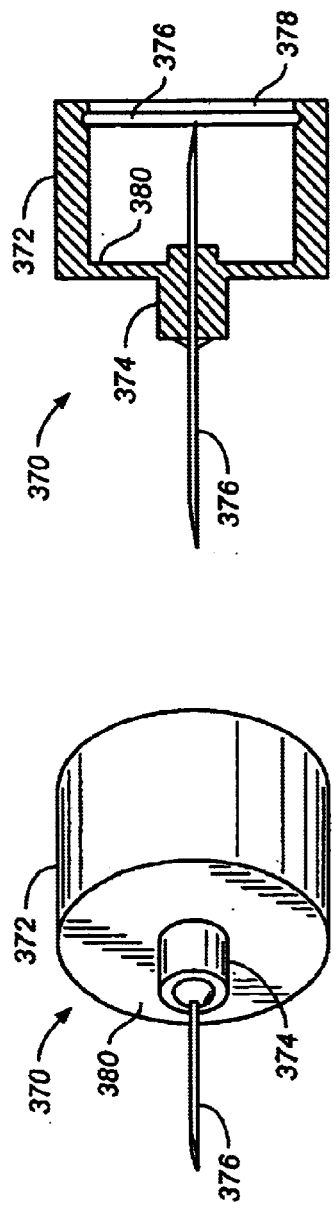
FIG._21
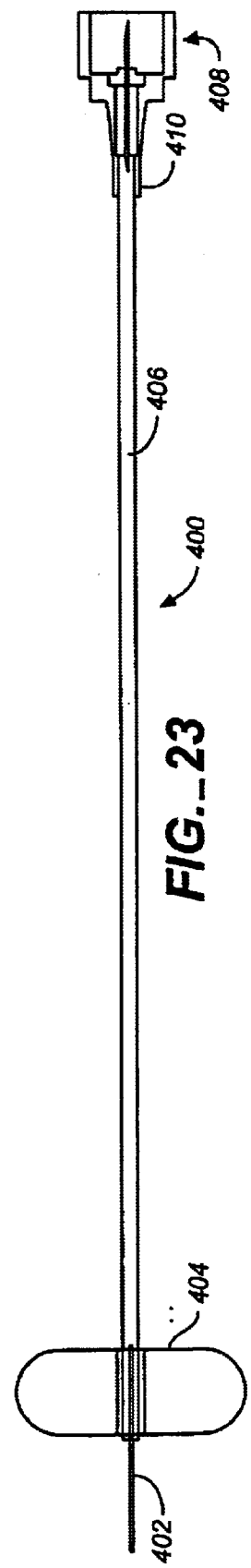
FIG._23

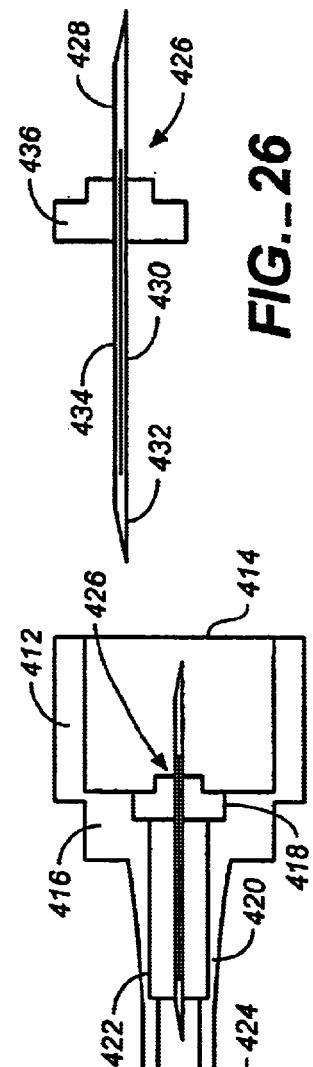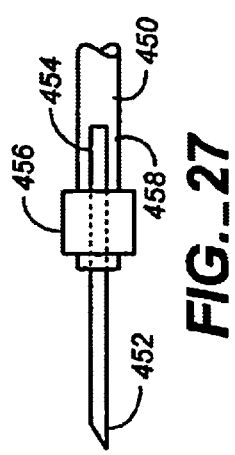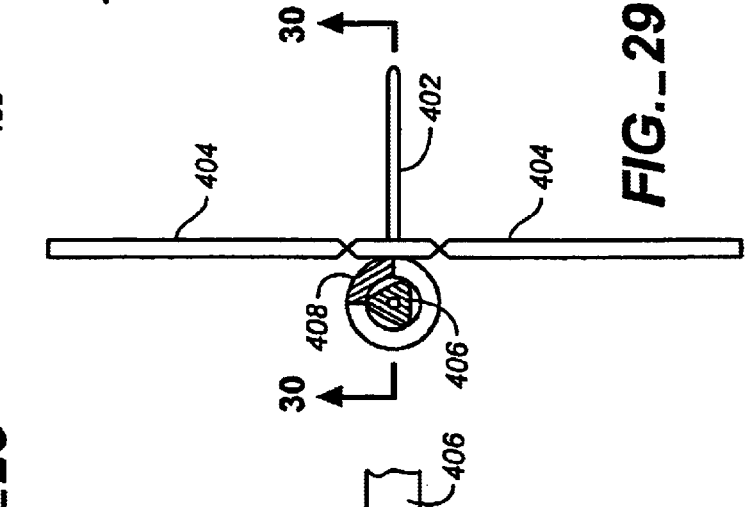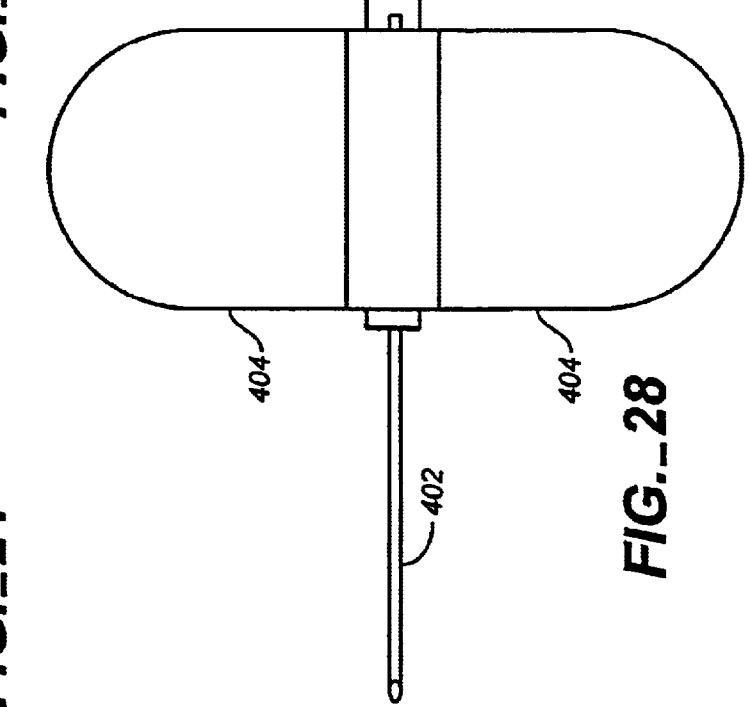

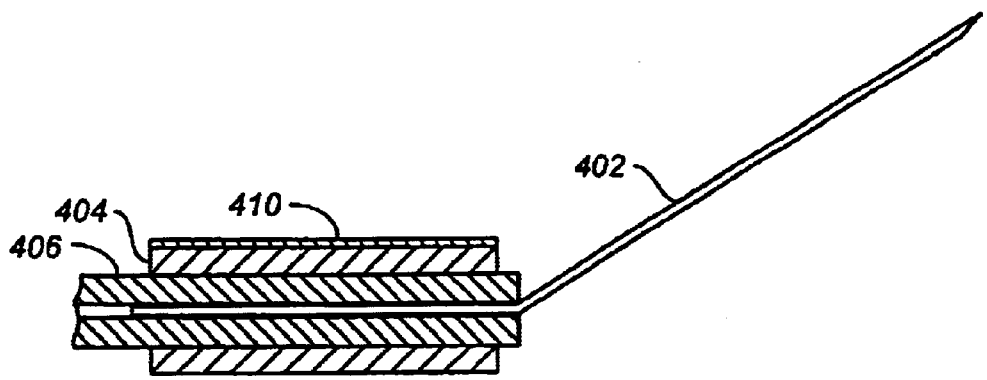
FIG._30
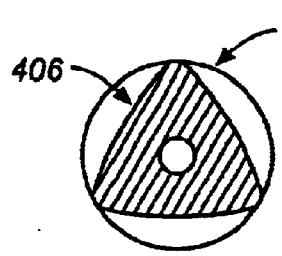 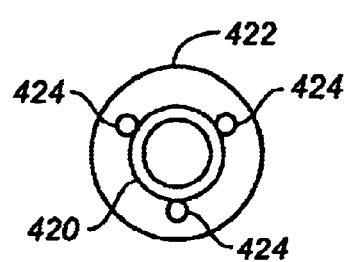 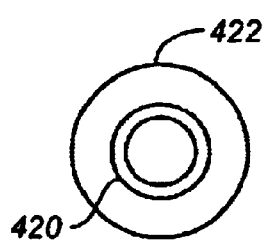
FIG._31     FIG._32     FIG._33
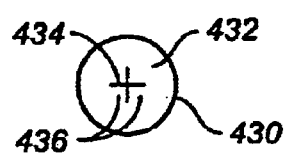 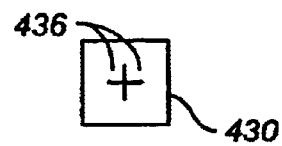
FIG._34     FIG._35

SUBCUTANEOUS INJECTION SET FOR USE WITH A RESERVOIR THAT HAS A SEPTUM

The present application is related and claimed priority to U.S. application Ser. No. 60/195,702, filed Apr. 7, 2000, by Joel Douglas, U.S. application Ser. No. 60/188,624, filed Mar. 13, 2000, by Joel Douglas, and U.S. application Ser. No. 60/176,538, filed Jan. 18, 2000, by Joel Douglas, the entire contents of each of which is incorporated by reference herein.

BACKGROUND OF THE INVENTION

1. Field of the Invention

The present invention relates to medical connectors and infusion sets.

2. Brief Description of the Related Art

In general, whenever a therapeutic fluid is to be delivered subcutaneously to a patient form an external source, a passageway, such as that provided by a hollow needle or other type of cannula or catheter device, must be first inserted through the skin of the patient in order to provide a passageway or channel through which the fluid may pass from its source external to the patient to the desired subcutaneous location under the skin of the patient. Once this passageway has been installed, the desired infusion system may be used in conjunction with an appropriate catheter connecting the external source of fluid with the passageway leading to the subcutaneous delivery point to deliver the fluid to the patient at an appropriate delivery rate.

Unfortunately, several problems associated with infusing fluids into the patient as described above are usually encountered. Most systems require the patient to use a syringe that is fitted with a thread or luer fitting. The patient must fill the syringe and attach the catheter to it. However, in doing so the medication can become contaminated and is therefore no longer sterile. Non-sterile solutions can lead to infection. In addition the inconvenience of having to fill the syringe in the first place, and then attach and prime the catheter is difficult for many patients.

In the early 1990's prefilled insulin cartridges were first introduced by insulin manufacturing companies for use in insulin pens. These cartridges are prefilled and make their use very convenient for the patient. The difficulty is that the prefilled cartridges need to have a septum to allow the medication to remain sterile.

The recent popularity of insulin infusion pumps as an alternative to multiple daily injections for insulin-dependent diabetics requires the use of such an injection set to deliver insulin from a small, portable insulin infusion pump to the subcutaneous injection location. However, these devices require the patient to fill a syringe, which defeats the sterility of the mixture. Furthermore, there exists a substantial problem with the use of injection sets, as described above, in that flexible PVC is not completely insulin-compatible. This is in contrast to hard PVC, which is safe for use with insulin. While the exact nature of the reaction exhibited by insulin in contact with flexible PVC has not been determined with certainty, it is believed that the insulin, which is pH sensitive, reacts with $CO_2$, the flow of which therethrough is not inhibited by flexible PVC. In addition, the large quantities of plasticizer used in flexible PVC may result in a leaching problem when used with insulin.

Since flexible PVC is not a barrier for $CO_2$, the $CO_2$ which flows through the flexible PVC tubing will react with the insulin, causing the insulin to aggregate and to precipitate out of solution. Such precipitation of the insulin will likely cause clotting and blockage in the tube or in the needle, thereby inhibiting the flow of insulin to the subcutaneous depot.

Heat will also accelerate the clotting process of insulin in flexible PVC tubing without the pH change caused by $CO_2$. The reason for this has not been finally determined, but it may be due to zinc in the insulin forming zinc chloride. In any event, heat will further compound the situation faced by delivery of insulin through flexible PVC tubing.

The amount of insulin exiting the injection set will therefore vary considerably, with portions of the insulin becoming attached to the interior of the tube and eventually coating the interior of the tube, even if blockage does not occur. Over time, the situation will improve somewhat assuming blockage of the tube per se does not occur, but the amount of insulin actually delivered to the patient will vary considerable even with the best of circumstances. It may therefore be appreciated that the use of a flexible PVC tubing injection set to deliver insulin from an insulin infusion pump is neither desirable nor medically acceptable.

Other substances exhibit reactions when delivered through flexible PVC tubing. Lipids and proteins have adverse reactions with flexible PVC delivery systems, and nitroglycerin also reacts to some degree with a flexible PVC environment.

One solution which has been proposed to the problem has been through the use of polyethylene tubing, which does not cause a reaction with insulin passing therethrough. Polyethylene is a barrier to $CO_2$, and the major problem of $CO_2$ passing through the tubing is thereby eliminated. Additionally, the problem of clotting of the insulin due to heat is also substantially minimized.

Several problems have arisen with the use of epoxy bonded polyethylene infusion sets, all of which are due to the relative disadvantage of the epoxy bonding process to a solvent bonding process. First of all, an epoxy bond is simply not as strong as a solvent bond. Secondly, epoxy bonds have substantial aging problems, which limit shelf life of the injection set. Since the epoxy bond loses its mechanical bonding properties over time, the injection set will become less sturdy, with the potential for the tubing coming loose from the needle increasing substantially over time. Thirdly, batch control of epoxy used in epoxy bonding is time consuming and cumbersome. Finally, epoxy bonding or "potting" is a more expensive process than solvent bonding, resulting in a product having an economic disadvantage relative to a product made by solvent bonding.

It is thereby apparent that there exists a substantial need for an injection set for delivery of insulin (or other fluids exhibiting reactions when flowed through flexible PVC tubing), which injection set utilizes polyethylene tubing to inhibit reaction and subsequent degradation of insulin flowing therethrough.

SUMMARY OF THE INVENTION

According to a first exemplary embodiment, a medication infusion set comprises a base tube having an exterior surface, a proximal end, a distal end, and an inner lumen extending between the proximal and distal ends, the base tube formed of a material selected from the group consisting of polyethylene and polypropylene, a rigid cannula having a proximal end, a distal end, and a lumen extending between the proximal and distal ends, the cannula proximal end positioned in the base tube lumen, and a tube of a heat shrinkable material positioned on the base tube exterior surface at least in a region of the base tube in which the cannula is inserted, the heat shrinkable tube having been heat shrunk to the exterior of the base tube and compressing the base tube and the cannula together to form a seal.

According to a second exemplary embodiment, an infusion device comprises a housing including a proximal end, a distal end, two lateral sides, and a bore extending between the proximal end and the distal end, a soft cannula having a proximal end, a distal end, and a lumen extending between the proximal end and the distal end, the cannula positioned in part in the housing bore with the cannula distal end outside of the housing, and a locking device attached to a lateral side of the housing, the locking device including a locking finger and a lever, the lever extending distally and the locking finger extending proximally, the locking finger including a distally facing surface.

According to a third exemplary embodiment, a connecting device comprises a hub including a proximal end face, a distal end face, two lateral sides, and a bore extending between the proximal end and the distal end, rigid cannula including a proximal end, a distal end, and a lumen extending between the proximal end and the distal end, the rigid cannula mounted in the hub bore with the rigid cannula distal end exterior of the hub, a pin extending distally from the hub distal end face and offset laterally from the rigid cannula, and a proximally facing surface on one of the lateral sides positioned between the proximal end face and the distal end face.

According to a fourth exemplary embodiment, a process of forming a medical infusion set comprises the steps of inserting an end of a rigid cannula into the lumen of a length of tubing, and heat shrinking a tube of heat shrinkable material over the portion of the tubing in which the end of the rigid cannula is positioned to compress the tubing onto the rigid cannula.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which FIG. 1 illustrates a perspective view of a first embodiment of an infusion set and connector in accordance with the present invention;

FIG. 2 illustrates a longitudinal cross-sectional view of the set of FIG. 1;

FIGS. 3 and 4 illustrate top plan views, with portions broken away in FIG. 4, of another embodiment of an infusion set in accordance with the present invention FIG. 5 is a top plan view of a portion of the devices illustrated in FIG. 4;

FIG. 6 is a front elevational view of the device in FIG. 5;

FIG. 7 is a rear (upsidedown) elevational view of the device in FIG. 5;

FIG. 8 is a left side elevational view of the device in FIG. 5;

FIG. 9 is a cross-sectional view, taken at line 9—9 in FIG. 5;

FIGS. 10 and 11 illustrate enlarged views of portions of the device illustrated in FIG. 5;

FIG. 12 illustrates a top plan view of a portion of the device illustrated in FIG. 4;

FIG. 13 illustrates a side elevational (upsidedown) view of the portion in FIG. 12;

FIG. 13a illustrates another portion of the device in FIG. 12;

FIG. 14 illustrates a front elevational view of the device in FIG. 12;

FIG. 15 illustrates a top plan view of an insertion device in accordance with the present invention;

FIG. 16 illustrates a side elevational view of the device illustrated in FIG. 15;

FIG. 17 illustrates a top plan view of a plug in accordance with the present invention;

FIG. 18 illustrates a front elevational view of the plug illustrated in FIG. 17;

FIG. 19 illustrates a cross-sectional view taken at line 19—19 in FIG. 18;

FIG. 20 illustrates a longitudinal cross-sectional view of a cannula in accordance with the present invention;

FIG. 21 illustrates a perspective view of a pen needle in accordance with the present invention;

FIG. 22 illustrates a longitudinal cross-sectional view of the pen needle illustrated in FIG. 21;

FIG. 23 illustrates yet another device in accordance with the present invention;

FIG. 24 illustrates a perspective view of a portion of the device illustrated in FIG. 23;

FIG. 25 illustrates a longitudinal cross-sectional view of the portion of FIG. 24;

FIG. 26 illustrates a portion of the device illustrated in FIG. 25;

FIG. 27 illustrates yet another aspect of the present invention;

FIG. 28 illustrates an enlarged top plan view of a portion of the device illustrated in FIG. 23;

FIG. 29 illustrates a side view, partially in cross-section, of the portion illustrated in FIG. 28;

FIG. 30 illustrates a longitudinal cross-sectional view along line 30—30 in FIG. 29;

FIG. 31 illustrates a cross-sectional view of a tube in another aspect of the present invention;

FIGS. 32 and 33 illustrate yet further aspects of the invention; and

FIGS. 34 and 35 illustrate portions of a device in accordance with the present invention.

DESCRIPTION OF THE PREFERRED EMBODIMENTS

Referring to the drawing figures, like reference numerals designate identical or corresponding elements throughout the several figures.

The present invention relates to a disposable injection set that offers the ability for the patient to infuse from a prefilled insulin cartridge without compromising the sterility of medication to be infused. Also, utilization of prefilled medication cartridges to provide a source of infusion material makes it easy and convenient to use by the average patient. The utilization of a cannula to pierce the septum of the medication cartridge provides the sterile means for connecting the catheter to the cartridge and by combining it with the soft or flexible catheter with needles fixed on both ends permits the development of a convenient and sterile infusion device. The cannula that is inserted into the skin of a patient is held at its insertion location with a low profile holding pad or housing. The opposite end has a threaded connector with a cannula fixed in it that permits communication between the fluid in the reservoir and the catheter. The cannula on the threaded connector is positioned so that the tubing of the catheter is fixed over the cannula and attached by adhesive to the catheter tubing. The adhesive is selected from a set of epoxies or solvent adhesive that are capable of bonding to the soft tubing. The adhesive needs to create the appropriate bond and be capable of being sterilized. The solvent bondable shrink tube is then placed over the end of the tube and heated to produce a secure joint, and the adhesive is applied to the outer surface of the shrink tube and inserted into the connector.

Turning now to the drawing figures, FIGS. 1 and 2 illustrates a perspective view and a longitudinal cross-sectional view, respectively, of a first embodiment 100 of an infusion apparatus in accordance with the present invention. Generally, the apparatus 100 includes a medication delivery device 102, into which a medication ampule 108 is releasably installed, and a catheter infusion set 104. The medication delivery device 102 can be any of numerous such devices which receive a medication ampule 108, including "pen" type injectors, programmable medication pumps, and those described in U.S. application Ser. No. 60/156,535, filed Sep. 29, 1999, U.S. application Ser. No. 60/170,570, filed Dec. 13, 1999, U.S. application Ser. No. 60/177,762, filed Jan. 24, 2000, and filed Sep. 29, 2000, "Reusable Medication Delivery Device", to Joel Douglas et al., the entire contents of each of which are incorporated by reference herein.

The device 102 includes a holder 106 which releasably holds the medication ampule 108 therein so that the ampule's septum 112 is exposed and accessible to be pierced and accessed in a known fashion. Similarly, the piston 110 of the ampule 108 is accessible so that it can be moved to expel medication from the ampule, again in a known fashion. The device 102 includes external threads 114 so that a medical connector, described in greater detail below, can be releasably attached to the device to access the ampule's contents through the septum 112.

The catheter infusion set 104 includes a proximal connector 116 having a cylindrical collar or shroud 118, which has internal threads 120 which mate with external threads 114. A piercing element 122, e.g., a needle, extends proximally from the connector 116. A distal catheter, cannula, needle, or other tubular element 124 extends from the distal end of the set 104, and is in fluid communication with the piercing element 122 via a tube 130. As can be seen in FIG. 1, the catheter 124 extends at an angle a to the longitudinal axis of the device (when laid straight). Angle a is preferably between about 15 degrees and about 90 degrees, and more preferably is about 30 degrees, so that the catheter can reside comfortably in the subcutaneous tissue layers of a patient. A holding pad 126 having an adhesive face 128 is connected to the catheter 124 by any of numerous ways, preferably by an adhesive 136 (see FIG. 2). At the proximal end of the set 104, the tube 130 is secured to a distal portion 138 of the connector 116.

As discussed above, the materials used for tube 130 effect the way that the connection between the tube and the connector 116 can be made. According to one aspect of the present invention, a tube 132 is heat shrunk over the exterior of the tube 130 in the area where the distal portions of piercing element 122 extend into the lumen of the tube 130. In one aspect of the invention, the tube 132 secures the piercing element 122 and the tube 130 together. In another aspect, the tube 132 presents an outer surface to which the distal portions 138 of the connector 116 can be solvent bonded, as at 134, which outer surface is different from that of the tube 130. The tube 132 can extend only a short way distally along tube 130, or can extend distally along the entire length of tube 130. According to other aspects of the present invention, tube 132 can be formed of any of a number of materials which permits good solvent bonding to the connector 116, such as PVC, polyester, or PTFE.

The operation of the exemplary embodiment of the present invention described above and illustrated in FIGS. 1 and 2 will now be described with reference thereto. A user or patient inserts a medication ampule 108, such an insulin cartridge, into the delivery device 102, with the ampule's septum 112 accessible through the device. The collar 116 is screwed or otherwise placed over the end of the device 102 so that the piercing element 122 pierces the septum 112 and places the interior of the ampule in fluid communication with the cannula 124. The user can then prime the set 104, if desired. If the set 104 is already in place subcutaneously, the user manipulates the device 102 to move the piston 110 to deliver an amount of medication to the patient through the cannula 124.

FIGS. 3 and 4 illustrate top plan views, with portions broken away in FIG. 4, of another embodiment 200 of an infusion set in accordance with the present invention. Set 200 includes a cannula housing 202 which holds a soft cannula 204 for positioning subcutaneously in a patient. A connecting hub 206 is releasably positioned to the proximal end of the cannula housing 202. A length of tubing 208 preferably flexible, is secured to the proximal portions of the connecting hub. A proximal connector 210 is secured to the proximal end of the tubing 208. The connector 210 includes a cylndrical collar or shroud 212, a hub 222, and a piercing element 214. A distal portion 226 of the piercing element 214 extends proximally through the hub 222 and is in fluid communication with the tubing 208. An extension 216 of the connector 210 extends around the proximal portions of the tubing 208 and connects the tubing to the connector 210. In one aspect of the present invention, a shrink tube, such as tube 132 described above, is inserted into extension 216 to facilitate bonding.

The connecting hub 206 includes distally extending pins 216, 218 which are inserted into and mate with complementarily placed and configured holes or bores in the cannula housing 202, described in greater detail below. A distally extending hollow tube 220 extends from the connecting hub 206, and includes proximal portions 224 which are in fluid communication with tubing 208. The proximal portions 224 can be secured to the tubing 208 in any suitable manner, including utilizing a shrink tube such as tube 132 and solvent bonding. Hollow tube 220 may be sharpened at its distal most end, e.g., be a needle, or can alternatively be blunt.

Turning now to FIGS. 5–9, several views of the cannula housing 202 are illustrated. Specifically, FIG. 5 is a top plan view of the cannula housing; FIG. 6 is a front elevational view; FIG. 7 is a rear (upsidedown) elevational view; FIG. 8 is a left side elevational view; and FIG. 9 is a cross-sectional view, taken at line 9—9 in FIG. 5.

The cannular housing 202 include a generally frustoconical, distally extending portion 230, through which a bore 232 extends. The bore 232 is widened at its distal end to form a cannula recess 234, for reasons which will be discussed further below. The proximal end of the bore 232 widens in a frustoconically shaped proximal portion 236. The proximal portion 236 is tapered in order to guide a tube, such as tube 220, when inserted into the bore 232 through proximal opening 238. The housing 202 also includes blind bores for receiving the pins from the connecting hub. When there are two pins, 216 and 218 as illustrated in FIG. 3, there are two such blind bores 244, 246, which are sized and positioned to receive the pins. As will be readily appreciated by one of ordinary skill in the art, while one such pin-bore combination is less preferable because it guides the housing 202 and hub 206 together less effectively, and more than two pin-bore combinations may provide better registration between the hub and the housing, any number of pins and bores are within the spirit and scope of the present invention.

The proximal end of the housing 202 includes a pair of guide extensions 242, one on each lateral side of the housing, which together delimit an open proximal space 240 sized and shaped to receive portions of the connecting hub 206. Each guide extension 242 includes an laterally inwardly directed, slightly tapered guide surface 248, 250. The guide surfaces 248, 250 are sized and oriented so that they provide initial guidance to the outer surfaces of the hub 206 when the hub and housing 202 are brought together, described in greater detail below.

The housing also includes at least one, and preferably two locks 252, 254, positioned on the lateral sides of the housing. The locks 252, 254 are provided to releasably lock the hub 206 to the housing 202 when the hub and housing are properly mated together (see FIG. 4). The locks 252, 254 include releasable locking fingers 256, 258 which extend proximally from regions where the locks join with the housing 202. The fingers 256, 258 include a locking bearing surface 260 which is distally directed for bearing against portions of the hub 206 which face proximally (again, see FIG. 4). Adjacent to the locking bearing surface(s) 260, each finger 256, 258 is provided with an angled cam surface 262. The cam surfaces provide a place for the connecting hub 206 to bear against the fingers 256, 258 and push them laterally outward, to spread the fingers and permit the connecting hub to enter the space 240 when moved distally relative to the housing 202.

The locks 252, 254 also include levers 264 ion their proximal ends, opposite the fingers 256, 258. The cantilevered levers 264 are positioned laterally spaced from the housing 202 so that there are spaces 266 between the levers and the housing into which the levers can be flexed. Flexure of the levers 264 laterally inward cause the fingers 256, 258 to flex laterally outward, thus permitting the connecting hub 206 to enter and exit the space 240 more easily. As will be readily appreciated by one of ordinary skill in the art, pulling proximally on the connecting hub 206, when positioned in the space 240, with sufficient force will also result in the fingers 256, 258 spreading apart and the hub being released from the housing 202 and the locks 252, 254.

As illustrated in FIGS. 6, 8, and 9, the soft cannula 204, in some aspects of the present invention, is angled relative to the bottom surface 268 of the housing 202 at an angle β, wherein β can be any acute angle, and can be the same as α.

FIGS. 10 and 11 illustrate enlarged views of portions of the connecting hub 206. Specifically, FIG. 10 illustrates the locks 254, including the channel 270 between the finger 258 and the housing 202. FIG. 11 illustrates the bore 232, without the soft cannula 204 positioned in the bore.

FIGS. 12–13a illustrate the connecting hub 206. More specifically, FIG. 12 illustrates a top plan view of the connecting hub 206; FIG. 13 illustrates a side elevational (upsidedown) view; FIG. 13a illustrates a portion of the hub; and FIG. 14 illustrates a front elevational view. As discussed above, pins 216, 218 and tube 220 extend from the hub 206. The hub 206 includes locking surfaces 280 which are oriented and positioned so that the bearing,surfaces 260 of the locking fingers 256, 258 will bear against the locking surfaces 280 when the hub is positioned in the space 240. Cam surfaces 282 are also provided on the distal end of the hub 206 to bear against the cam surfaces 262 of the fingers 256, 258, as described above.

The hub 206 includes a proximal portion 284 to which the tubing 208 is attached, preferably in a permanent manner. A longitudinally extending lumen or bore 286 extends from the proximal end to the distal end of the hub 206. The lumen is sized to receive the tubing 208 therein, with the proximal end 224 of the tube 220 in fluid communication with the lumen of the tubing. Although a straight bore 286 can be used, it is preferable that the bore include a shoulder 292 along its length, with a proximal portion 288 and an intermediate portion 290 on either side of the shoulder. The intermediate portion 290 can be of a smaller inner diameter than the proximal portion 288 so that the tubing 208 is radially compressed. Intermediate portion 290 can also have a slightly tapered inner diameter, so that the radial compression of the tubing is greater at the shoulder than elsewhere along the bore 286. The bore 286 also includes a distal portion 296, in which a needle hub or positioning block 294 is mounted.

FIG. 13a illustrates that, in one aspect of the invention, the block 294 can have a beveled side 300 to assist in aligning the tube 220 at the same angle as the soft cannula 204. FIGS. 13 and 14 illustrate that the hub 206 can optionally have a slanted top surface 298.

FIGS. 15 and 16 illustrate a top plan view and a side elevational view, respectively, of an insertion device 302 used to insert the soft cannula into the patient, preferably subcutaneously The device 302 includes a needle or stylet 304 extending distally from an insertion handle 306. The insertion handle 306 is substantially the same shape and size as the hub 206, and includes a pair of pins 308, 310, substantially similar to pins 216, 218 . The needle or stylet 304 is of a length so that the sharpened distalmost end of the needle or stylet extends beyond the distalmost end of the soft cannula 204 when the insertion handle 306 is mounted on the housing 202, in the same manner as the connecting hub 206 is mounted to the housing in FIG. 4. A proximal end of the needle or stylet 304 is preferably within the handle 306. According to yet another aspect of the present invention, the needle 304 can include a score line 314 along its length so that the needle can be broken off and used as an infusion needle. The handle 306 would then require a lumen similar to lumen 286 in FIG. 12.

FIGS. 17–19 illustrate several views of a plug in accordance with one aspect of the present invention. More specifically, FIG. 17 illustrates a top plan view of a plug 330; FIG. 18 illustrates a front elevational view of the plug, and FIG. 19 illustrates a cross-sectional view taken at line 19—19 in FIG. 18. The outside size and shape of plug 330 is the same as the insertion handle 306 and the connecting hub 206, described above. The plug 330 includes a pair of pins 332, 334 to mate with blind bores 244, 246, described above. The plug 330 includes a central plugging element 336 having a preferably conical or frustoconical tip 338 extending distally from the plugging element 336. The plugging element 336 is formed of a somewhat soft material which is somewhat compressible, so that when the plug 330 is mounted to the housing 220 in the manner of hub 206 and handle 306, the plugging element will enter into and seal the proximal portions of bore 232. By way of example and not of limitation, element 338 can be formed of a medical grade silicon rubber. Thus, the plug 330 can be used to seal the bore 232, and therefore access to the patient's body by dirt and pathogens is greatly restricted when connecting hub 206 is disconnected from the housing 202.

The size and taper of plugging element 336 and tip 338 are preferably selected to plug and seal with tapered portion 236, although the size and taper can also be selected to seal and plug the bore 232 at the junction of bore 232 and taper 236, the junction of taper 236 and proximal opening 238, the opening 238 itself, or any combination of these structures by forming plugging element 336 with a complementary shape. According to yet another aspect of the present invention, the material out of which plugging element 336 is formed can be doped with an antimicrobial or similar compound to inhibit the growth of microorganisms on the plugging element itself or on the surfaces against which it seats.

FIG. 20 illustrates a cross-sectional view of soft cannula 204. The soft cannula 204 includes a longitudinally extending lumen 350, which extends between a proximal end 352 and a distal end 354. A positioning and retention bead, ring, or lug 356 is formed on the outer surface of the cannula 204, and is sized to fit into recess 234 of the housing 202. The bead 356, in one aspect of the present invention, is sized relative to the recess 234 so that the bead can securely hold the cannula 204 in the housing 202. In another aspect of the present invention, the bead 356 assists in positioning the distal end 354 of the cannula 204 at a predetermined distance from the housing 202. In yet another aspect of the present invention, the cannula 204 is permanently mounted in the bore 232 by any of numerous ways, such as solvent or adhesive bonding, ultrasonic welding, heat staking, or the like.

The cannula 204, in yet another aspect of the present invention, includes a restriction surface 358 formed on the inner surface of the lumen 350 near or at the proximal end 352 of the cannula. The restriction surface 358 is formed by a reduction in the inner diameter of the lumen 350 to a diameter which is only slightly smaller to slightly larger than the outer diameter of tube 220. By forming the inner diameter of the lumen 350 and the outer diameter of tube 220, and optionally of needle or stylet 304, so that they are nearly the same, the clearance between the two surfaces is too small for liquids such as blood and aqueous solutions of medications to flow. According to yet another aspect of the present invention, the change in diameter can be formed on the outside of the tube 220, and optionally on the outside of needle or stylet 304. Thus, one aspect of the present invention is a seal against the passage of fluid in and out of the housing 202 along the cannula 204, other than through the lumen 350.

The operation of the exemplary embodiment of the present invention described above and illustrated in FIGS. 3–20 will now be described with reference thereto. The operation of the set 200 is similar in many respects to set 104. Initially, the housing 202 is mounted to the handle 306 so that the distal end of the needle or stylet 304 extends distally from the distal end of the soft cannula 204. As discussed above, the restriction 358 and the external surface of the needle or stylet 304 provide a fluid seal. The flaps 436 of the dust door 430 have been previously pushed aside by the needle or stylet 304. The soft cannula 204 and housing 202 can then be inserted into a patient, e.g., subcutaneously, in a manner well-appreciated by one of ordinary skill in the art. The handle 306 is then retracted proximally by pressing laterally inwardly on one or both of the levers 264, which releases the handle from the housing 202. The flags 436 return to their generally planar configuration, inhibiting dust and dirt from entering the device.

The connecting hub 206, with the tubing 208 and connector 210, is then inserted into the space 240, laterally displacing the locking fingers 256, 258. With the pins 216, 218 in the bores 244, 246, the guide surfaces 248, 250 guide the outer surfaces of the hub 206 as the hub moves distally. The locking fingers 256, 258 then snap over the locking surfaces 280, securing the hub 206 to the housing 202 with the tube 220 extending through the soft cannula 202. The outer surface of the tube 220 and the restriction 358 form a fluid seal, as described, and the flaps 436 again are moved aside by the tube 220. The connector 210 can then be attached to a septum of a medication ampule, and medication delivered through the tubing 208, through the soft cannula 202, and to the patient.

After the medication infusion described above, the hub 206 can be removed proximally by pressing on the levers 264, as described above, to release the hub from the housing 202. The plug 330 can then be installed in place, as described above, with the plugging element 338 moving aside the flaps 436 and forming a seal with one of the proximal structures of the housing 202. The housing 202 and cannula 204 are then prepared for later infusion, while sterility of the site is enhanced or maintained.

FIGS. 21 and 22 illustrate a pen needle 370 according to yet another aspect of the present invention. FIG. 21 illustrates a perspective view of the pen needle 370; FIG. 22 illustrates a longitudinal cross-sectional view. The pen needle 370 includes a cylindrical collar or shroud 372 having an open end 378, a hub 374 forming a part of a closed end 380 of the collar, and a two-ended needle 376 extending through the hub with one end within the collar. The pen needle 370 also includes an annular groove 376 formed in the inner surface of the collar, and receives in the groove a dust door described in greater detail below. The pen needle 370 can be used in the place of set 104, described above with reference to FIGS. 1 and 2, by placing the collar 372 around the septum of an ampule so that the needle 376 pierces the septum. The other end of the needle 376 can be inserted into a patient, and an infusion of medication delivered to the patient.

FIG. 23 illustrates yet another infusion set 400 in accordance with other aspects of the present invention. The infusion set 400 can be used with a medication delivery device 102 as described above which includes a medication ampule having a septum. The infusion set 400 includes an infusion needle or cannula 402 at a distal end, a holding pad 404 to secure the infusion needle to a patient, tubing 406 extending proximally from and in fluid communication with the infusion needle 402, and a proximal connector 408 connected to the proximal end of the tubing. As discussed in greater detail above, the tubing 406 may be attached to the proximal connector using shrink tubing and solvent bonding, for example.

FIGS. 24–26 illustrate details of the infusion set 400 of FIG. 23. More specifically, FIG. 24 illustrates a perspective view of the connector 408; FIG. 25 illustrates a longitudinal cross-sectional view of the connector; and FIG. 26 illustrates a portion of the connector. The connector 408 includes a cylindrical collar or shroud 412 which has an open end 414 and a closed end 416. An annular shoulder 418 is formed in the closed end 416, and a distal tubular extension 420 extends distally from the closed end. The extension 420 includes a lumen 422 communicating the open portion of the collar 412 with the distal end of the connector. The lumen 422 can have a constant inner diameter, or can include a distal reduced inner diameter portion 424 which, as described above with reference to bore 286, can assist in forming a seal with the tubing 406 when the tubing is inserted into the lumen 422. A fluid transfer device 426 is mounted in the connector 408 in the annular shoulder 418, and is secured to the connector, such as by glueing, ultrasonic welding, or the like.

Turning to FIG. 26, the fluid transfer device 426 includes a sharpened proximal end 428 to pierce a septum of a medication ampule, such as septum 112. The distal end 432 of the shaft 430 can be either sharpened or blunt. A lumen 434 extends between the sharpened proximal 428 and distal 432 ends. A mounting block 436 is mounted to the shaft 430, and has a size and a shape to fit to annular shoulder 418.

FIG. 27 illustrates, in a manner similar to FIG. 2, how a tube 450 can be joined to a needle or rigid cannula 452. With the end of the needle 454 within the lumen 458 of the tube 450, a tube 456 of shrinkable material is positioned over the outside of the tube so that it overlaps both the tube and the needle. By shrinking the tube 456, the tube 450 is clamped down onto the shank of the needle 452, securing the two together. Thereafter, the outer surface of the tube 456 can be used to secure the assembly to another component, such as by solvent bonding.

FIG. 28 illustrates a top plan view of the distal infusion end of set 400, FIG. 29 illustrates a side view, partially in section of the distal end of set 400, and FIG. 30 illustrates a cross-section view taken at line 30—30 in FIG. 29. As can be seen in FIG. 29, tubing 406 is formed to be kink-resistant, as described in greater detail below. A hub 438 fluidly communicates the tubing 406 with the needle or cannula 402. FIG. 30 illustrates that the holding pads 404 include an outer adhesive layer 410, to secure the device to a patient.

FIG. 31 illustrates a cross-sectional view of tubing 406 according to one aspect of the present invention. The tubing 406 is formed to have a cross-sectional shape that makes the tubing resistant to kinking. In FIG. 31, the tubing 406 has a triangular cross-section. A piece of shrink tube 422 is illustrated positioned around the tube 406 prior to being shrunk down onto the outer surface of the tubing, for the reasons presented herein. By way of example and not of limitation, inner tube 406 can be formed of a polyethylene or polypropylene, and the outer shrink tube 422 can be formed of a PVC, polyester, or PTFE. FIGS. 32 and 33 illustrate yet further aspects of the present invention. In FIG. 32, tubing 406 is formed of a base tube 420, a shrink tube 422 around the base tube, and at least one filaments, wires, or the like 424 between the base tube and the shrink tube. The filaments 424 strengthen the tube and assist in preventing kinking. In FIG. 33, the filaments 424 have been removed, with the shrink tube 422 acting to assist in preventing kinking. The shrink tube is 422 is then shrunk over the base tube 420, resulting in a strengthened tubing 406.

FIGS. 34 and 35 illustrate a dust door 430 according to yet another aspect of the present invention. The door 430 is formed of a thin sheet 432 of relatively strong and pliable material, which includes intersecting slits 434 which together form two or more flaps 436. By way of example and not of limitation, sheet 432 can be formed of Mylar of about 0.003 inches thickness. The door 430 is, in certain aspects of the present invention, preferably installed in opening 238, 378, or the open end of collar 116, and prevents dust and dirt from entering these openings. Referring to FIG. 5 and opening 238, when it is desired to insert, for example, tube 220 into the bore 232, the flaps 436 are pushed aside by the advancing tube 220 without interfering with assembly of the device and without piercing the flaps. When the tube 220 is retracted, the flaps 436 resume their generally planar configuration.

The operation of the exemplary embodiment of the present invention described above and illustrated in FIGS. 23–35 will now be described with reference thereto. The use of the embodiments of FIGS. 23–35 is similar to the use of the embodiments of FIGS. 1 and 2. A user or patient inserts a medication ampule 108, such an insulin cartridge, into the delivery device 102, with the ampule's septum 112 accessible through the device. The connector 408 is screwed or otherwise placed over the end of the device 102 so that the piercing element 428 pierces the septum 112 and places the interior of the ampule in fluid communication with the cannula 402. The user can then prime the set 400, if desired. If the set 400 is already in place subcutaneously, the user manipulates the device 102 to move the piston 110 to deliver an amount of medication to the patient through the cannula 124.

While the invention has been described in detail with reference to preferred embodiments thereof, it will be apparent to one skilled in the art that various changes can be made, and equivalents employed, without departing from the scope of the invention.

What is claimed is:

1. An infusion device comprising:
   a housing including a proximal end, a distal end, two lateral sides, and a bore extending between the proximal end and the distal end;
   a soft cannula having a proximal end, a distal end, and a lumen extending between the proximal end and the distal end, the cannula positioned in part within the housing bore with an end of the cannula extending outside of the housing in a first direction;
   a locking device attached to a lateral side of the housing, the locking device including a locking finger and a lever, the lever extending in the first direction and the locking finger extending in a direction opposite to the first direction, the locking finger including a distally facing surface.

2. An infusion device in accordance with claim 1, wherein the soft cannula lumen has a first inner diameter and a second smaller inner diameter, the second inner diameter being in a region adjacent the cannula proximal end.

3. An infusion device in accordance with claim 1, wherein the soft cannula further comprises an exterior surface and a bead extending from the exterior surface between the proximal and distal ends.

* * * * *

UNITED STATES PATENT AND TRADEMARK OFFICE
CERTIFICATE OF CORRECTION

PATENT NO. : 6,749,589 B1
DATED : June 15, 2004
INVENTOR(S) : Joel S. Douglas et al.

It is certified that error appears in the above-identified patent and that said Letters Patent is hereby corrected as shown below:

Title page,
Item [73], Assignee, after the word "Sterling", please delete "Medication" and insert -- Medivations --.

Signed and Sealed this

Fifteenth Day of February, 2005

JON W. DUDAS
*Director of the United States Patent and Trademark Office*